United States Patent

Harada et al.

Patent Number: 5,853,867
Date of Patent: Dec. 29, 1998

[54] ABSORBENT COMPOSITE, METHOD FOR PRODUCTION THEREOF, AND ABSORBENT ARTICLE

[75] Inventors: Nobuyuki Harada, Osaka; Yoshihiro Motono, Hyogo; Shigeru Sakamoto, Osaka; Toshimasa Kitayama, Hyogo, all of Japan

[73] Assignee: Nippon Shokubai Co., Ltd., Osaka, Japan

[21] Appl. No.: 713,866

[22] Filed: Sep. 13, 1996

[30] Foreign Application Priority Data

Sep. 14, 1995 [JP] Japan .................................. 7-237358
Jul. 12, 1996 [JP] Japan .................................. 8-183816

[51] Int. Cl.$^6$ .................................................. A61F 13/15
[52] U.S. Cl. ...................... 428/317.9; 428/913; 442/153; 442/167; 442/168; 442/171; 604/366; 604/367; 604/372; 604/374; 604/377
[58] Field of Search .................... 428/317.9, 913; 442/153, 167, 168, 171; 604/366, 367, 372, 374, 377

[56] References Cited

U.S. PATENT DOCUMENTS 5,124,188  6/1992  Roe et al. ................................. 428/72

FOREIGN PATENT DOCUMENTS

| 2-289608 | 11/1990 | Japan . |
| 3-162855 | 7/1991 | Japan . |
| 5-200064 | 8/1993 | Japan . |
| WO 81/03274 | 11/1981 | WIPO . |
| WO 94/04351 | 3/1994 | WIPO . |
| WO 94/04352 | 3/1994 | WIPO . |

*Primary Examiner*—Helen L. Pezzuto
*Attorney, Agent, or Firm*—Burns, Doane, Swecker & Mathis, LLP

[57] ABSTRACT

This invention concerns an absorbent composite a supporting member and a cationic absorbent polymer and anionic absorbent polymer particles fixed to the supporting member. This absorbent composite excels in absorbing capacity under pressure, vertical aspiration power, and flexibility and suffers only sparing exfoliation of an absorbent polymer. This invention further concerns an absorbent composite which contains an absorbent polymer in an amount of at least 30% by weight based on the total weight of the absorbent composite and, after absorbing a liquid, shows a value of not less than 3 for the expansion anisotropy specified by the following formula.

$$\text{Expansion anisotropy} = (Ez/Ex + Ez/Ey)/2$$

(wherein Ex, Ey, and Ez respectively represent coefficient of liner expansion in the directions of X axis, Y axis, and Z axis) and an absorbent article using the absorbent composite.

This invention permits production of a novel absorbent composite which suffers no leakage and excels in water absorbing power, water retaining power, and flexibility and an absorbent article using the absorbent composite.

26 Claims, 1 Drawing Sheet

ABSORBENT COMPOSITE, METHOD FOR PRODUCTION THEREOF, AND ABSORBENT ARTICLE

BACKGROUND OF THE INVENTION

1. Field of the Invention

This invention relates to a novel absorbent composite, a method for the production thereof, and an absorbent article. More particularly, this invention relates to an absorbent composite which excels in absorbing capacity under pressure, vertical aspiration power, and flexibility and suffers no easy exfoliation of an absorbent polymer, a method for the production thereof, and an absorbent article.

2. Description of the Prior Art

In recent years, numerous absorbent sheets of the type which are produced by depositing a monomer on a fibrous substrate by spraying or spreading and then polymerizing the monomer thereby fixing an anionic absorbent polymer so fast on the substrate as to prevent the polymer from being exfoliated from or migrated in the substrate in consequence of the absorption of water have been introduced to the art. These absorbent sheets prevent the exfoliation of polymer to a certain extent and enjoy improvement in the ability to retain the shape of sheet. They cannot be applied for actual use, however, because an effort to heighten the glass transition temperature of the absorbent article or absorbent composite and exalt the concentration of the anionic absorbent polymer results in adding to the rigidity of the absorbent article or absorbent composite in spite of an increase in the capacity for absorbing water. When the method of manufacture mentioned above expects the absorbent sheet to retain flexibility, it has no alternative but to lower the proportion of the absorbent polymer contained in the absorbent sheet. The absorbent sheet to be produced, therefore, is precluded from acquiring a fully satisfactory capacity for absorbing water by the lower absorbent polymer content in the sheet coupled with the restriction imposed by the fibers of the sheet on the expansion of the absorbent polymer.

WO94/04351 and WO94/04352 disclose a technique for fixing an absorbent polymer with a binder on a fibrous substrate. This method indeed produces an absorbent sheet in which the absorbent polymer is not restrained from swelling by the fibrous substrate. Since the proportion of the absorbent polymer to be contained in the absorbent sheet has its limit, the absorbent composite which is obtained at all by this method has an insufficient total capacity for absorbing water. The absorbent composite fails to manifest the ability of water absorption as designed because the absorbent polymer which is in a granular form undergoes exfoliation from and migration in the absorbent sheet. When the absorbent composite is used in a disposable diaper and exposed to a vigorous motion such as is often generated by a baby wearing the diaper, it incurs the problem that the absorbent composite will be broken and the diaper will suffer consequent leakage.

In the conventional absorbent articles such as sanitary napkins and disposable diapers, the absorbent polymer is used more often than not in combination with pulp, a substance having a high speed of absorption, because it absorbs bodily humor at a limited speed and does not absorb the bodily humor until it is wetted with the bodily humor. The pulp in an absorbent article, though exhibiting compression and recovery from a bend to a certain extent when it is dry, suffers extreme loss of strength and shows practically no recovery of strength when it is wet. The conventional absorbent article, therefore, has the problem that when the absorbent article wet with a bodily humor is exposed to complicate stress due to the motion of a human body, the pulp deforms to impart twist and warp to the absorbent article and the bodily humor flows along the twist and induces the absorbent article to suffer from the phenomenon of lateral leakage of liquid. Further, the pulp, when wetted with the bodily humor, incurs a decrease of bulk, with the result that a gap will be formed between the absorbent article and the human body and the phenomenon of leakage will similarly ensue.

Thus, various studies have been made to date with a view to solving the problems of the prior art mentioned above. For example, JP-B-03-67,712 discloses a method for incorporating in an absorbent article an absorbent polymer fixed in the shape of a sheet on a supporting member thereby preventing the absorbent particle from being twisted and warped by the stress which is exerted while it is worn by a user. The sheet of the absorbent polymer, however, exhibits low expansion anisotropy after absorbing water and remains yet to be improved in the fastness of adhesion between the absorbent article and the human body. JP-A-03-162,855 and JP-A-02-289,608 disclose such absorbent articles as use therein cellulose sponge or polyurethane foam possessed of expansion anisotropy and consequently enjoy improvement in speed of absorption and fastness of adhesion to a human body. These methods invariably utilizes the elastic recovery force which the compressed sponge or foam manifests on contacting water. The absorbent polymer contained in this absorbent article is utilized only for absorbing and retaining the water temporarily retained on the sponge or foam which is deficient in ability to retain water. It makes virtually no contribution to the expansion of the absorbent article itself. The absorbent article, therefore, is at a disadvantage in suffering deficiency in the absorbing power under an increased pressure, a quality necessary for such absorbent articles as disposable diapers. Moreover, it has been very difficult to have the absorbent polymer dispersed at a high concentration and fixed in the sponge or foam so as to ensure manifestation of expansion anisotropy and, at the same time, avoid impairing flexibility of the absorbent article.

The present invention, produced in view of such problems of the prior art as mentioned above, has for an object thereof the provision of a novel absorbent composite, a method for the production thereof, and an absorbent article.

Another object of this invention is to provide an absorbent composite which excels in absorbing capacity under pressure, vertical aspiration power, and flexibility and suffers no easy exfoliation of an absorbent polymer, a method for the production thereof, and an absorbent article.

Yet another object of this invention is to provide a novel absorbent composite which induces no leakage and an absorbent article using the absorbent composite.

Still another object of this invention is to provide a novel absorbent composite which excels in water absorbing power, water retaining power, and flexibility and possesses the function to expand specifically in one direction and an absorbent article using this absorbent composite.

SUMMARY OF THE INVENTION

The objects mentioned above are fulfilled by the absorbent composite, the method for the production thereof, and the absorbent article according to the present invention.

Specifically, this invention concerns an absorbent composite which comprises a supporting member and a cationic absorbent polymer and anionic absorbent polymer particles fixed to the supporting member.

This invention further concerns an absorbent composite wherein the anionic absorbent polymer particles are fixed through the medium of the cationic absorbent polymer to the supporting member.

This invention further concerns an absorbent composite wherein the amount of the cationic absorbent polymer is in the range of 1–10,000 parts by weight, based on 100 parts by weight of the supporting member and the amount of the anionic absorbent polymer particles is in the range of 10–10,000 parts by weight, based on 100 parts by weight of the cationic absorbent polymer.

This invention further concerns an absorbent composite wherein the supporting member is a fibrous substance.

This invention further concerns an absorbent composite in the shape of a sheet having a volume of at least 5 cm$^2$, a thickness of not less than 0.2 mm, and a density in the range of 0.3–1.1 g/cm$^3$ and exhibiting a vertical aspiration power of not less than 5 cm, a absorbing capacity under pressure of not less than 20 g/g, and Gurley stiffness of not more than 1000 mgfN.

This invention further concerns an absorbent composite wherein the proportion of the absorbent polymer is not less than 80% by weight, based on the total weight of said absorbent composite.

This invention further concerns an absorbent composite containing at least 30% by weight of absorbent polymer based on the total weight of the absorbent composite and characterized in that the absorbent composite, on absorbing a liquid, shows a value of not less than 3 for the expansion anisotropy specified by the following formula.

$$\text{Expansion anisotropy} = (Ez/Ex + Ez/Ey)/2$$

(wherein Ex, Ey, and Ez respectively represent coefficient of liner expansion in the directions of X axis, Y axis, and Z axis).

This invention further concerns an absorbent composite wherein the expansion anisotropy is not less than 5.

This invention further concerns an absorbent composite wherein the absorbent polymer is fixed through the medium of the absorbent binder to the supporting member and compressed in the direction of thickness of the absorbent composite.

This invention further concerns an absorbent composite wherein the absorbent binder exhibits a retaining capacity of not less than 5 g/g after undergoing centrifugal separation of physiological saline solution.

This invention further concerns an absorbent composite wherein the absorbent binder is a cationic absorbent polymer and the absorbent polymer is an anionic absorbent polymer.

This invention further concerns an absorbent article which comprises an absorbent composite set forth in the preceding inventions.

This invention further concerns a method for the production of an absorbent composite, which is characterized by depositing a raw material monomer capable of forming a cationic absorbent polymer on a supporting member, polymerizing or polycondensing the raw material monomer thereby fixing a cationic absorbent polymer to the supporting member, and fixing anionic absorbent polymer particles to the cationic absorbent polymer.

This method further concerns a method for the production of the absorbent composite, wherein the amount of the cationic absorbent polymer is in the range of 1–10,000 parts by weight, based on 100 parts by weight of the supporting member and the amount of the anionic absorbent polymer particles is in the range of 10–10,000 parts by weight, based on 100 parts by weight of the cationic absorbent polymer.

This invention further concerns a method for the production of the absorbent composite, wherein the supporting member is a fibrous substance.

This invention further concerns a method for the production of the absorbent composite, wherein the fibrous substance is a fibrous sheet.

This invention further concerns a method for the production of the absorbent composite, wherein the anionic absorbent polymer particles are scattered on the fibrous sheet having the cationic absorbent polymer fixed in advance thereon and then the scattered particles are pressed against the fibrous sheet.

DESCRIPTION OF PREFERRED EMBODIMENT

Figure 1:
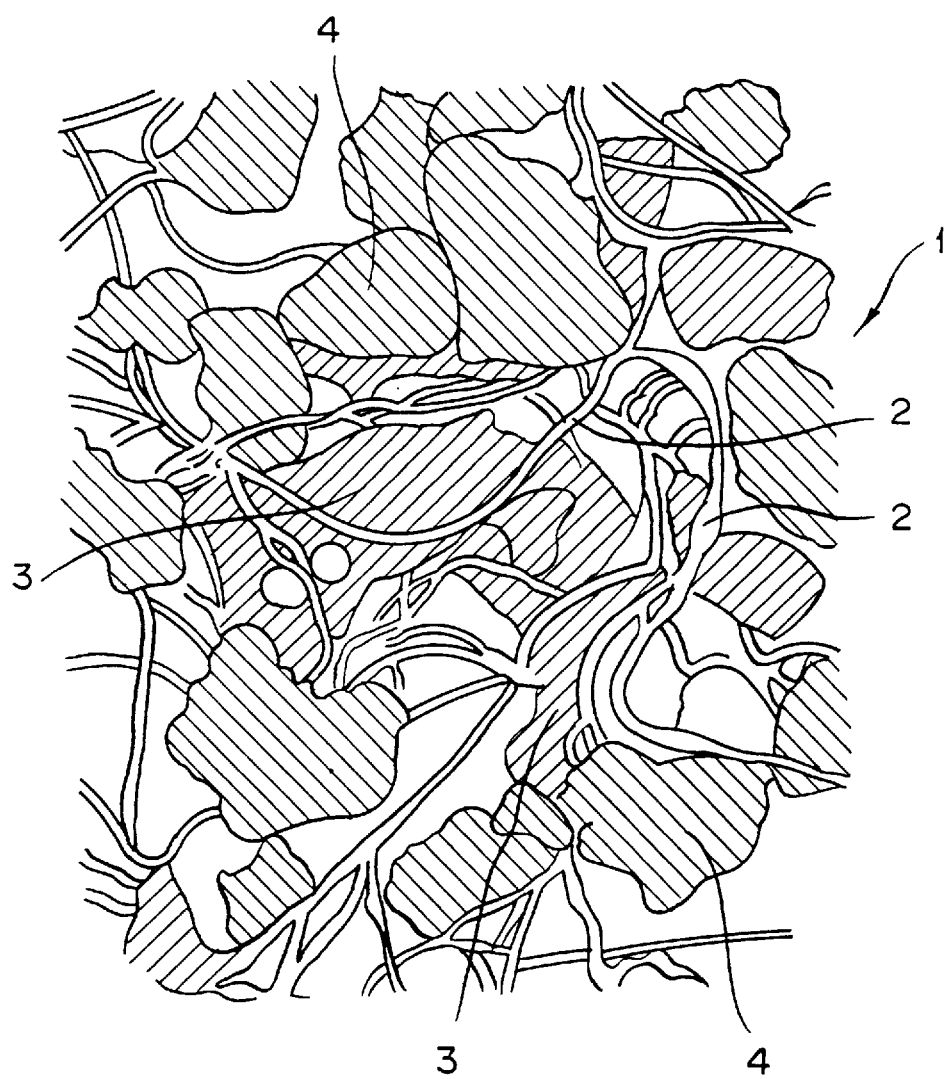
FIG. 1 is a schematic diagram as an aid in describing the structure of an absorbent composite according to this invention.

The first absorbent composite of this invention comprises a supporting member and a cationic absorbent polymer and anionic absorbent polymer particles fixed thereto.

The supporting member to be used in this invention may be in numerous forms such as, for example, foam like foamed polyurethane, powder, granules, sheet, ribbons, fibers, and combinations thereof. Among other forms mentioned above, the form of fibers proves appropriate for the supporting member. As the fibrous supporting member, fibrous webs made of natural or synthetic fibers or natural or synthetic pulp, particularly fibrous sheets, are advantageously used. The fibrous sheets include woven fabric, non-woven fabric, paper, and knit fabric, for example. Non-woven fabrics made of various kinds of fibrous webs prove advantageous. Fibers of both the hydrophilic and the hydrophobic type are equally usable. The hydrophilic fibers include wood pulp, cotton, wool, rayon, acetate, and vinylon, for example. The hydrophobic fibers include polyester, acrylic, nylon, polyethylene, polypropylene, and polyvinyl chloride, for example. Various mixed fibers formed of the various fibers mentioned above are also usable. The fibrous sheets include those of the shape of a tape, for example. Though the tapes of fibrous sheets have no particularly limited thickness, those of a thickness in the range of 0.01–100 mm, preferably 0.1–10 mm, are appropriately used. Elongates of fibrous sheet can be produced by continuously feeding a fibrous sheet. They allow the absorbent composite contemplated by this invention to be produced with high operational efficiency. Properly, the fibers have a diameter in the range of 0.1–1,000 $\mu$m, preferably in the range of 1–100 $\mu$m.

The cationic absorbent polymers which are effectively used in this invention include Mannich reaction products of polyallyl amine, polyalkylene polyamine, polyethylene imine, polyvinyl amine, and poly(meth)acryl amide, homopolymers of poly(meth)acryl amine and dialkylaminoalkyl (meth)acrylate and copolymers thereof with (meth)acryl amide, homopolymers of quaternized ammonium salts of dialkylaminoalkyl (meth)acrylates obtained by the treatment with a halogenated alkyl (such as, for example, methyl chloride, ethyl chloride, or methyl bromide) and copolymers of such homopolymers with a (meth)acrylamide, quaternized ammonium salts of polydialkylallyl amines, polymers of quaternized vinyl-benzyl amines, acetylated chitosan, and condensation products of epichlorohydrin with polyamines or monoamines, for example. The binder obtained by adding a cross-linking agent to such a polymer either during or after polymerization and cross-linking the polymer is a polycation possessing numerous cationic groups. This binder is advantageously used because it forms a strong ionic bond with an anionic absorbent polymer and retains strong adhesive force after absorbing water and swelling with water. The cross-linked polycation proves particularly advantageous when it has a glass transition point which is lower than normal room temperature.

The halogenated alkyl quaternary salts of dialkylamino (meth)acrylates which are effectively used for the production of the polymers mentioned above include the halogenated alkyl quaternary salts of such monomers as N,N'-dimethylaminoethyl (meth)acrylate, N,N-dimethylaminopropyl(meth)acrylate, N,N-diethylaminobutyl(meth)acrylate, N,N-diethylaminoethyl (meth)acrylate, and N,N-diethylaminopropyl(meth)acrylate, for example. In this invention, such a cationic absorbent polymer after polymerization may be applied in a suitable liquid form such as, for example, a solution by means of spraying or spreading to the supporting member and fixed thereto. Preferably, the fixation of this cationic absorbent polymer to the supporting member is attained by causing a corresponding monomer or a mixture of the monomer to be deposited in the form of an aqueous solution on the supporting member by means of impregnation, for example, and polymerizing or polycondensing the applied layer of the monomer solution.

The polymerization of the monomer or monomer mixture solution is carried out in the presence of a polymerization initiator at a temperature in the range of 0°–200° C., preferably 50°–150° C.

As concrete examples of the polymerization initiator which is advantageously used herein, oxidizing or azo type radical polymerization initiators which are soluble in water or miscible and dispersible in water maybe cited. The oxidizing polymerization initiators include persulfates such as sodiumpersulfate, potassium persulfate, and ammonium persulfate; hydrogen peroxide; and organic peroxides such as ditertiary butyl peroxide and acetyl peroxide, for example. The azo type polymerization initiators include azo compounds such as 2,2'-azobis (2-amidino propane) dihydrochloride, 2,2'-azobis(N,N'-dimethyleneisobutyl amidine) dihydrochloride, and 4,4'-azobis (4-cyanovaleric acid), for example.

It is permissible, when necessary, to use an oxidizing polymerization initiator and an azo type polymerization initiator in combination, use simultaneously a plurality of polymerization initiators selected from the group mentioned above, or use such a polymerization initiator as mixed with such a reducing substance as a sulfite or L-ascorbic acid to effect redox polymerization. The polymerization initiator is used in an amount in the range of 0.001–10% by weight, preferably 0.01–1% by weight, based on the total amount of the monomer.

The monomer, when necessary, incorporates therein a cross-linking agent in an amount in the range of 0.0001–10% by weight, preferably 0.01–2% by weight, based on the total amount of the monomer. The cross-linking agent to be effectively used in this case is a compound which has two or more unsaturated double bonds in the molecular unit thereof. As concrete examples of the cross-linking agent which answer the description, N,N'-methylenebis(meth) acryl amide, (poly)ethylene glycol di(meth)acrylate, (poly) propylene glycol di(meth)acrylate, trimethylol propane tri (meth)acrylate, trimethylol propane di(meth)acrylate, glycerin tri(meth)acrylate, glycerin acrylate and methacrylate, ethylene oxide-modified trimethylol propane tri(meth)acrylate, pentaerythritol tetra(meth)acrylate, dipentaerythritol hexa(meth)acrylate, triallyl cyanurate, triallyl isocyanurate, triallyl phosphate, triallyl amine, poly(meth) allyloxy alkanes, glycidyl(meth)acrylate, N-methylol acrylamide, (poly)ethylene glycol diglycidyl ether, and glycerol diglycidyl ether may be cited.

In this invention, the amount of the cationic absorbent polymer to be fixed to the supporting member is in the range of 1–10,000 parts by weight, preferably 10–5,000 parts by weight, and most preferably 50–1,000 parts by weight, based on 100 parts by weight of the supporting member.

The anionic absorbent polymer to be used in this invention is the homopolymer or copolymer of such a water-soluble ethylenically unsaturated monomer as shown below. As concrete examples of the monomer, acrylic acid, methacrylic acid, 2-(meth)acryloyl ethane sulfonic acid, 2-(meth) acryloyl propane sulfonic acid, 2-(meth)acrylamide-2-methyl propane sulfonic acid, vinyl sulfonic acid, (meth) allyl sulfonic acid, and alkali metal salts and ammonium salts of such acids may be cited. These monomers may be used either singly or in the form of a mixture of two or more members. Acrylic acid and salts thereof are preferred examples.

The monomer, when necessary, may incorporate therein a cross-linking agent in an amount in the range of 0.0001–10% by weight, preferably 0.01–2% by weight. The cross-linking agent is a compound having two or more unsaturated double bonds in the molecular unit thereof. As concrete examples of the monomer which answer the description, N,N'-methylenebis(meth)acryl amide, (poly) ethylene glycol di(meth)acrylate, (poly)propylene glycol di(meth) acrylate, trimethylol propane tri(meth)acrylate, trimethylol propane di(meth)acrylate, glycerin tri(meth) acrylate, glycerin acrylate and methacrylate, ethylene oxide-modified trimethylol propane tri(meth)acrylate, pentaerythritol tetra(meth)acrylate, dipentaerythritol hexa (meth)acrylate, triallyl cyanurate, triallyl isocyanurate, triallyl phosphate, triallyl amine, poly(meth)allyloxy alkanes, glycidyl(meth)acrylate, N-methylol acrylamide, (poly) ethylene glycol diglycidyl ether, glycerol diglycidyl ether, ethylene glycol, polyethylene glycol, propylene glycol, glycerin, pentaerythritol, ethylene diamine, polyethylene imine, and aluminum sulfate may be cited.

In this invention, the anionic absorbent polymer is obtained by preparatorily polymerizing the corresponding monomer in a polymerization vessel and, when necessary, drying and pulverizing the resultant polymer. Specifically, the monomer or a mixture thereof is prepared in the form of an aqueous solution and then subjected to polymerization in the polymerization vessel in the presence of a polymerization initiator at a temperature in the range of 0°–200° C., preferably 50°–150° C.

As concrete examples of the polymerization initiator which is advantageously used herein, oxidizing or azo type radical polymerization initiators which are soluble in water or miscible and dispersible in water may be cited. The oxidizing polymerization initiators include persulfates such as sodium persulfate, potassium persulfate, and ammonium persulfate; hydrogen peroxide; and organic peroxides such as ditertiary butyl peroxide and acetyl peroxide, for example. The azo type polymerization initiators include azo compounds such as 2,2'-azobis(2-amidinopropane) dihydrochloride, 2,2'-azobis(N,N'- dimethyleneisobutylamidine) dihydrochloride, and 4,4'-azobis(4-cyanovaleric acid), for example.

It is permissible, when necessary, to use an oxidizing polymerization initiator and an azo type polymerization initiator in combination, use simultaneously a plurality of polymerization initiators selected from the group mentioned above, or use such a polymerization initiator as mixed with such a reducing substance as a sulfite or L-ascorbic acid to effect redox polymerization. The polymerization initiator is used in an amount in the range of 0.001–10% by weight, preferably 0.01–1% by weight, based on the total amount of the monomer.

The anionic absorbent polymer particles consequently obtained have an average particle diameter in the range of 1,000–10 μm, preferably 600–100 μm.

The anionic absorbent polymer particles which are obtained as described above are uniformly dispersed by a suitable means such as scattering on the supporting member to which the cationic absorbent polymer particles have been fixed as described above and then are fixed by such means as pressing to the surface of the cationic absorbent polymer. The amount of the anionic absorbent polymer particles to be used for this purpose is in the range of 10–10,000 parts by weight, preferably 100–1,000 parts by weight, based on 100 parts by weight of the cationic absorbent polymer.

With reference to FIG. 1, in an absorbent composite 1 using a supporting member of fibers 2 and obtained as described above, a cationic absorbent polymer 3 is fixed to the fibers 2 and anionic absorbent polymer particles 4 are fixed through the medium of the cationic absorbent polymer 3 to the fibers 2.

Appropriately, the first absorbent composite according to this invention is in the form of a sheet having a volume of at least 5 cm$^3$, preferably 10–200 cm$^3$, a thickness of not less than 0.2 mm, preferably 0.5–5 mm, and a density in the range of 0.3–1.1 g/cm$^3$, preferably 0.3–1.0 g/cm$^3$ and exhibiting vertical aspiration power of not less than 5 cm, preferably 6.5–10 cm, absorbing capacity under pressure of not less than 20 g/g, preferably 24–50 g/g, and Gurley stiffness of not less than 1000 mgfN, preferably 0–500 mgfN.

The amount of the absorbent polymer (total of cationic absorbent polymer and anionic absorbent polymer) appropriately is not less than 80% by weight, preferably 85–99% by weight, based on the amount of the absorbent composite. By setting this amount at a level above 80% by weight, it is made possible to decrease the amount of the supporting member and compact the absorbent composite to be produced.

The second absorbent composite of this invention is characterized by containing at least 30% by weight of the absorbent polymer based on the total amount of the absorbent composite and exhibiting a value of not less than 3 for the expansion anisotropy specified by the following formula after absorbing a liquid.

$$\text{Expansion anisotropy} = (Ez/Ex + Ez/Ey)/2$$

(wherein Ex, Ey, and Ez respectively represent coefficient of liner expansion in the directions of X axis, Y axis, and Z axis).

The expansion anisotropy which is determined by the method to be described herein below is an index of the degree with which a given absorbent composite, after absorbing a liquid, expands in the direction of Z axis relative to the directions of X axis and Y axis. The second absorbent composite, after absorbing a liquid, exhibits anisotropy in the voluminal expansion, namely expands mainly in the direction of thickness of the composite. Since the absorbent composite, when wetted with a bodily humor, does not decrease but rather increases its bulk, it permits production of an absorbent article which gains in fitness to the contour of a human body and precludes leakage when it is wetted. If the absorbent composite has a number of less than 3 for the expansion anisotropy mentioned above, it will fail to acquire fully satisfactory fitness to the human body. Preferably, the absorbent composite has a number of more than 5 for the expansion anisotropy.

The second absorbent composite of this invention contains the absorbent polymer in an amount of not less than 30% by weight based on the total weight thereof. By setting the amount of the absorbent polymer at a level above 30% by weight, the absorbent composite is enabled to acquire improved expansion anisotropy and absorbing power and the absorbent article incorporating therein the absorbing composite is enabled to enjoy a decrease in thickness and compaction in bulk. Appropriately, the amount of the absorbent polymer is in the range of 80–99% by weight.

The absorbent polymer to be used in this invention comprises an absorbent binder serving the purpose of fixing the absorbent polymer to the supporting member besides the absorbent polymer used in the absorbent composite which will be described in detail herein below. To be specific, cross-linked or not cross-linked hydrophilic natural and synthetic macromolecular compounds can be used. The natural macromolecular compounds include starch type and cellulose type compounds, for example. The synthetic macromolecular compounds include polyacrylic acid type and polyacrylate type compounds, polyvinyl alcohol type compounds, polyacryl amide type compounds, and polyoxyethylene type compounds, for example. Among other macromolecular compounds cited above, polyacrylate type and polyacryl amide type macromolecular compounds prove advantageous.

The second absorbent composite of this invention, for example, is in a structure such that the absorbent polymer is fixed through the medium of the absorbent binder to the supporting member and compressed in the direction of thickness.

The supporting member preferably has an compression coefficient of elasticity of not less than 60%. Particularly, the supporting member having a three-dimensional backbond structure or an open-cell structure is at an advantage in exhibiting strong recovery power after absorbing water. If the compression coefficient of elasticity is less than 60%, the disadvantage ensues that the supporting member will exhibit weak recovery power after absorbing water and will prevent the absorbent composite from attaining high expansion anisotropy.

The absorbent binder has close bearing on the flexibility of the absorbent composite because it discharges the part of causing adhesion and fixation of the supporting member, the absorbent polymer, and the binder. Preferably, the binder has flexibility. To be specific, a cross-linked polycondensate having a glass transition point lower than room temperature is advantageously used as the absorbent binder. The binder properly is possessed in itself of an ability to expand after absorbing water. By adopting the binder possessed of the ability to expand after absorbing water, the absorbent composite to be produced is enabled to acquire improved expansion anisotropy, further attain outstanding water absorbing power, water retaining power, and flexibility and, at the same time, enjoy an increase in the amount of the absorbent polymer used therein and a proportionate decrease in the amount of the supporting member. The produced absorbent composite, therefore, enjoys a decrease in thickness. Specifically, the absorbent binder properly exhibits a retaining capacity of not less than 5 g/g after the treatment of centrifugal separation of physiological saline solution. This retaining capacity which is determined by a method which will be described in detail herein below is an index for rating the water retaining property of a given absorbent composite. If the absorbent binder has a retaining capacity of less than 5 g/g, the disadvantage ensues that the absorbent binder will neither allow improvement in expansion anisotropy and absorbing power nor make any contribution to the decrease in thickness of the absorbent composite. Advantageously, the cationic absorbent polymer mentioned above is used as the absorbent binder of the quality under discussion.

The absorbent polymers which are effectively used herein include homopolymers and copolymers of water-soluble ethylenically unsaturated monomers, for example. Preferably, the anionic absorbent polymers mentioned above are used as the monomers for the homopolymers or copolymers.

As the second absorbent composite of this invention, therefore, the first absorbent composite of this invention described above is appropriately used.

For the purpose of enabling the second absorbent composite of this invention to be endowed with further exalted expansion anisotropy, it is advantageous that this second absorbent composite is obtained by further pressing the first absorbent composite or superposing a plurality of first absorbent composites and pressing the superposed layers. Though the superposition of the plurality of absorbent composites is attained by simply pressing the individual layers, their fast union may be accomplished, when necessary, by heating the interfaces of the superposed layers.

For the purpose of enabling the second absorbent composite to acquire hydrophilicity in the proximity of the surface thereof and diffuse and absorb a liquid at an exalted speed, it is proper that minute hydrophilic fibers are deposited in the proximity of the surface of the absorbent composite. The minute hydrophilic fibers effectively used herein include cellulose powder and milled fibers, for example. The amount of the minute hydrophilic fibers to be deposited is appropriately in the range of 0.01–5% by weight based on the total weight of the absorbent composite. If the amount of the minute hydrophilic fibers so deposited is less than 0.01% by weight, the effect of the addition of the minute hydrophilic fibers aimed at will not be obtained. If this amount exceeds 5% by weight, the disadvantage ensues that the amount of rewet will increase to the extent of heightening the cost of the absorbent composite.

Properly, the second absorbent composite of this invention has a retaining capacity of not less than 10 g/g after the treatment of centrifugal separation of physiological saline solution mentioned above. If the absorbent composite exhibits retaining capacity less than 10 g/g, the absorbent composite will be deficient in expansion anisotropy and absorbing power and, when used in an absorbent article, will fail to enhance the performance of the absorbent article.

The second absorbent composite of this invention which has been manufactured by the method described above has a structure such that the absorbent polymer is fixed through the medium of a soft binder possessing ionic adhesive power inside an empty space of the supporting member exhibiting high compression coefficient of elasticity. The amount of the absorbent polymer contained in the structure is not less than 30% by weight based on the total weight of the structure.

When this structure is exposed to an aqueous liquid, the aqueous liquid is instantaneously diffused in the empty space in the supporting member and in the empty spaces between the supporting member and the absorbent polymer and the binder and retained therein. At the same time, the absorbent polymer begins to absorb water and expand, promote the effect mentioned above, and cause the structure to expand further. Since the absorbent polymer is fixed to the supporting member through the medium of the binder, it expands not equally in all the directions but in one fixed direction. Thus, the absorbent composite exhibits expansion anisotropy. Since the expanding power produced in the absorbent composite chiefly originates in the expansion of the absorbent polymer due to its absorption of water, the absorbent composite exhibits fully satisfactory expansion anisotropy and absorbing power even when it is in a high pressed state. In the absorbent composite which is composed of a plurality of compressed layers, the expansion anisotropy is exalted because the phenomenon just mentioned manifests more conspicuously.

The absorbent article contemplated by this invention has only to comprise a front sheet pervious to liquid, a rear sheet impervious to liquid, and the first or the second absorbent composite mentioned above interposed between the two sheets. It may incorporate therein such other materials as paper, fiber, and inorganic particles in an amount short of impairing the function of the absorbent composite. The front sheet imposes no restriction particularly but requires only to be pervious to liquid. Non-woven fabric, woven fabric, paper, gauze, etc., for example, are usable as materials for the front sheet. Among other materials suggested above, non-woven sheets made of synthetic fibers of polyethylene, polypropylene, polyester, polyamide, etc. are used particularly advantageously. The rear sheet imposes no restriction particularly but requires only to be impervious to liquid. Films made of synthetic resins such as of polyethylene, polypropylene, polyvinyl chloride, polyvinylidene chloride, and polyvinyl alcohol are advantageously used as materials for the rear sheet.

The uses found for the second absorbent composite of this invention are not restricted to such sanitary absorbent articles as mentioned above. The second absorbent composite can be applied for such products as functional materials and toys which are capable of making effective use of the expansion anisotropy of the absorbent composite.

Now, this invention will be described more specifically below with reference to referential examples, working examples, and comparative examples. It should be noted, however, that this invention is not limited to these examples. Wherever "parts" is mentioned in the following examples, it means "parts by weight" unless otherwise specified.

The absorption properties of the absorbent polymers or absorbent composites (or absorbent polymer sheets) which were obtained in the referential examples, working examples, and comparative examples were determined by the following methods.

(1) Retaining capacity

This property of absorbent polymer particles or absorbent composite was determined by securing a sample, 0.2 g in weight, placing the sample in a heat-sealed tea bag type pouch of non-woven fabric, 6 cm×6 cm in area, keeping the pouch containing the sample immersed in physiological saline solution (0.9% Sodium chloride solution) for 30 minutes, then centrifuging (250 G) the wet pouch for 3 minutes thereby expelling excess physiological saline solution, weighing the pouch (W1), and separately repeating the procedure on an empty pouch to find a blank weight (W0). The retaining capacity (g/g) was found by subtracting the blank weight (W0) from the sample weight (W1) and dividing the difference by the weight (0.2 g) of the absorbent polymer particles or absorbent composite.

(2) Absorbing capacity under pressure

In the case of an absorbent polymer, this property was determined by placing a glass filer plate (G #1), 120 mm in diameter, in a glass petri dish, 160 mm in inside diameter and 20 mm in height, pouring an aqueous 0.4% saline solution (0.4% Sodium chloride solution) into the petri dish until it rose to the top of the glass filter plate, placing a filter paper (produced by Toyo Roshi K.K. and marketed under trademark designation of "FILTER PAPER No. 2") on the glass filter plate, then uniformly scattering 0.9 g of absorbent polymer particles in a cylindrical acrylic resin container, 60 cm in inside diameter and 60 cm in height, having a stainless steel net, 400 mesh, fixed in the bottom part thereof, further placing a load of 50 g/cm$^2$ inside the cylinder to complete a cylindrical aggregate, weighing (W1) the cylindrical aggregate, mounting this cylindrical aggregate on a filter paper, allowing the filter paper to absorb the aqueous 0.4% saline solution for 30 minutes, keeping the height of the aqueous 0.4% saline solution inside the petri dish at a fixed level during the progress of the absorption, and weighing (W2) the cylindrical aggregate after the 30 minutes standing. The absorbing capacity under pressure (g/g) was found by subtracting the weight (W1) from the weight (W2) and dividing the difference by the weight of the absorbent polymer (0.9 g) before the absorption mentioned above.

In the case of an absorbent composite, this property (g/g) was determined by repeating the procedure mentioned above while punching a sample, 3.1 cm×3.1 cm, from the absorbent composite, weighing the sample, placing this sample in the bottom part of the acrylic container, and adjusting the load to 50 g/cm$^2$.

(3) Absorption speed

This property was determined by punching a sample of the square of 1 inch (2.54 cm×2.54 cm) from a given absorbent composite, weighing the sample, pouring an aqueous 0.4% saline solution 10 times the weight of the sample into a polypropylene container, 5.5 cm in inside diameter and 1.5 cm in height, placing the square sample in the 0.4% saline solution, and clocking the time (in seconds) required for the solution to be wholly absorbed by the sample (namely until the solution ceased to form a pool on the sample tilted by 45 degrees). The time was reported as the absorption speed.

(4) Vertical aspiration power

This property was determined by cutting a sample of the shape of a ribbon, 2 cm×10 cm, from a given absorbent composite, suspending this sample vertically so that the leading end thereof would submerge to a depth of 2 mm in the bath of a physiological saline solution, allowing the suspended sample to absorb spontaneously the physiological saline solution vertically through the leading end thereof for 60 minutes, and thereafter measuring the distance (in cm) through which the solution was aspirated. This distance was reported as the vertical aspiration power.

(5) Flexibility

This property was determined by punching a sample of the shape of a strip, 2.54 cm×8.89 cm (1 inch×3.5 inches), from a given absorbent composite and, in a room kept at a temperature of 25° C. and a humidity of 50%, tested for flexibility in accordance with the method of determination of Gurley synthesis specified in JIS (Japanese Industrial Standard) L-1096. This sample was dried at a temperature of 70° C. for 3 hours and then tested for flexibility by following the same procedure.

(6) Compression coefficient of elasticity

This property of the supporting member of non-woven fabric in a given absorbent component was determined by punching three test pieces, 5 cm×5 cm, from the supporting member, superposing the three test pieces, measuring the superposed test pieces for thickness (T0) under an initial load of 7 g/cm$^2$ by means of a compression elasticity tester (pushing metal 5 cm) in conformity with the method specified in JIS L-1096, then allowing the superposed test pieces to stand under a load of 150 g/cm$^2$ for 1 minute, measuring them for thickness (T1), allowing them to stand under no load for 1 minute, then allowing them to stand under the same load, 7 g/cm$^2$, as the initial load, and measuring them for thickness (T2). The compression coefficient of elasticity (%) was calculated by the following equation using the results of the measurement. The determination of the compression coefficient of elasticity was carried out five times. The average of the results of the repeated determinations was reported as the Elasticity.

Compression coefficient of elasticity (%)=$\{(T2)-(T1)\}/\{(T0)-(T1)\} \times 100$ (7) Expansion anisotropy This property was determined by punching a test piece, 5 cm×5 cm, from a given absorbent composite, measuring the test piece for length in the direction of X axis (X0), length in the direction of Y axis (Y0), and length in the direction of Z axis (Z0), keeping the test piece immersed in a physiological saline solution for 30 minutes, then centrifuging (250 G) the sample for 3 minutes thereby expelling excess physiological saline solution, and measuring the expanded test pieces for lengths of X axis (X1), Y axis (Y1), and Z axis (Z1). The expansion anisotropy was calculated in accordance with the following formula.

Coefficient of liner expansion in the direction of X axis (Ex)=$(X1) \times (X0)$ Coefficient of liner expansion in the direction of Y axis (Ey)=$(Y1) \times (Y0)$ Coefficient of liner expansion in the direction of Z axis (Ez)=$(Z1) \times (Z0)$ Expansion anisotropy=$(Ez/Ex+Ez/Ey)/2$ (8) Absorption on inclined plane This test was carried out by cutting a sample sheet, 15 cm in length×7 cm in width, from a given absorbent composite, attaching the sample sheet to a surface tilted by 45 degrees, causing physiological saline solution to flow down the sample sheet from the upper end thereof at a rate of 7 ml/second, and allowing the sample sheet to absorb the flowing saline solution, clocking the duration (in seconds) between the time the flow of the saline solution was started and the time the flowing saline solution began to flow out of the lower end of the sample sheet and, at the same time, weighing (g) the saline solution absorbed by the sample sheet meanwhile.

(9) (Amount of) rewet (Examples 8–13 and Control 3–5)

For the determination of this magnitude, a simplified absorbent sheet was prepared by cutting a sample sheet, 12 cm×25 cm, from a given absorbent composite, cutting a sheet of the same size from the non-woven fabric extracted from a disposable infant grade diaper (produced by Procter & Gamble Far East Inc. and marketed under trademark designation of "Pampers"), and superposing the two sheets.

The simplified absorbent sheet was interposed between two acrylic sheets. The upper of the two superposed acrylic sheets was provided at the position corresponding to the central part of the simplified absorbent sheet with a liquid inlet tube, 23 mm in inside diameter, intended to permit introduction of an absorbent solution to the center of the simplified absorbent sheet. In the setup consequently obtained, the amount of rewet was determined by injecting 50 ml of physiological saline solution three times into the inlet tube at intervals of 30 minutes, removing the upper acrylic sheet 30 minutes after the end of the third injection, mounting a doubled total of 10 kitchen towels (produced by Shinoji Paper Co., Ltd. and marketed under trademark designation of "Nepia") of known black weight on the simplified absorbent sheet, keeping the kitchen towels for one minute under a load exerting a pressure of 57 g/cm$^2$ thereon, extracting the ten kitchen towels, and weighing them. The difference obtained by subtracting the blank weight from the weight obtained at the end of the test was reported as the rewet (g).

Referential Example 1

An aqueous monomer solution comprising 100 parts of quaternary salt of methyl chloride N,N-dimethylaminoethyl acrylate (aqueous 79% solution), 0.49 part of trimethylol propane triacrylate, 1.2 parts of hydroxyethyl cellulose, 0.29 part of sodium persulfate, and 45.5 parts of deionized water was applied at a rate of 96 g/m$^2$ to a non-woven polyester fabric, 2 mm in thickness, having a basis weight of 30 g/m$^2$ and an compression coefficient of elasticity of 72%. Then, the non-woven fabric having the aqueous monomer solution deposited thereon was kept for 10 minutes in an atmosphere of nitrogen at 100° C. for inducing the monomer to polymerize. Consequently, a cationic absorbent polymer sheet (1) having a cationic absorbent polymer fixed on the non-woven fabric was obtained. The cationic absorbent polymer sheet (1) was found to have a retaining capacity of 10 g/g.

Referential Examples 2–5

Four cationic absorbent polymer sheets (2)–(5) were obtained by repeating the procedure of Referential Example 1 while changing the amount of the aqueous monomer solution to be deposited respectively to 690 g/m$^2$, 290 g/m$^2$, 127 g/m$^2$, and 55 g/m$^2$. These cationic absorbent polymer sheets were found to have 11 g/g, 9 g/g, 10 g/g, and 3 g/g respectively as the magnitudes of retaining capacity.

Referential Example 6

In a nitrogen-sealed reaction vessel capable of releasing heat, 1.7 parts of trimethylol propane triacrylate was dissolved as a cross-linking agent in 5500 parts of an aqueous solution of sodium acrylate having a neutralization ratio of 75 mol % (monomer concentration 37%), the resultant solution was deaerated with nitrogen gas for 30 minutes, and the solution and 2.8 parts of ammonium persulfate and 0.14 part of L-ascorbic acid added thereto were left reacting at a temperature of 30°–70° C. for inducing the monomer to polymrize. The polymer formed 60 minutes after the start of polymerization was extracted as a hydrogel polymer divided into particles, about 5 mm in diameter. The particles of the hydrogel type polymer were spread on a metal net, 50 mesh, and dried with hot air at 150° C. for 90 minutes. The dried particles were pulverized with a roll type grinder to obtain anionic absorbent polymer (1) particles, 150 μm–850 μm in diameter. The anionic absorbent polymer (1) was found to have a retaining capacity of 35 g/g.

Referential Example 7

An anionic absorbent polymer (2) was obtained by mixing 100 parts of the anionic absorbent polymer (1) of Referential Example 6 with an aqueous cross-linking agent solution consisting of 0.5 part of glycerin, 2 parts of water, and 0.5 part of ethyl alcohol and heat-treating the resultant mixture at 196° C. for 4 minutes. The anionic absorbent polymer (2) was found to have a retaining capacity of 30 g/g and a absorbing capacity under pressure of 28 g/g.

Referential Example 8

In the same reaction vessel as used in Referential Example 6, absorbent polymer foam particles, 150–850 μm in particle diameter, were obtained by dissolving 5.2 parts by weight of polyethylene glycol diacrylate as a cross-linking agent in 5500 parts by weight of an aqueous solution of sodium acrylate having a neutralization ratio of 80 molt (monomer concentration 35%), deaerating the resultant solution with nitrogen gas for 30 minutes, adding 2.8 parts by weight of ammonium persulfate, 0.2 part by weight of 2-2'-azobis(2-methylpropionamidine) dihydro-chloride, and 0.14 part by weight of L-ascorbic acid to the resultant deaerated solution thereby inducing deposition of 2-2'-azobis(2-methylpropionamidine) diacrylate salt, and treating the resultant reaction mixture thereby inducing the monomer to polymerize under the same conditions as in Referential Example 6. An anionic absorbent polymer (3) was obtained by cross-linking the absorbent polymer particles in the same manner as in Referential Example 7. The anionic absorbent polymer (3) turned out to be foamed particles having a retaining capacity of 40 g/g and a absorbing capacity under pressure of 28 g/g and containing numerous air cells.

Example 1

An absorbent composite (1) of this invention was obtained by cutting a section, 10 cm×30 cm, from the cationic absorbent polymer sheet (1) obtained in Referential Example 1, adding the anionic absorbent polymer (1) of Referential Example 6 to the section throughout the entire volume thereof, and compressing the resultant composite under a pressure of 2 kg/cm$^2$. The absorbent composite (1) had a basis weight of 410 g/m$^2$, a thickness of 0.8 mm, a density of 0.49 g/cm$^2$, and a volume of 24 cm$^3$ and had the anionic absorbent polymer (1) deposited thereon in an amount of 327 g/m$^2$.

Example 2

An absorbent composite (2) of this invention was obtained by repeating the procedure of Example 1 while using the anionic absorbent polymer (2) of Referential Example 7 instead as an anionic absorbent polymer. The absorbent composite had a basis weight of 400 g/m$^2$, a thickness of 0.9 mm, a density of 0.46 g/cm$^3$, and a volume of 27 cm$^3$ and had the anionic absorbent polymer (2) deposited thereon in an amount of 317 g/m$^2$.

Example 3

An absorbent composite (3) of this invention was obtained by repeating the procedure of Example 2 while using the cationic absorbent polymer sheet (2) of Referential Example 2 instead as a cationic absorbent polymer sheet. The absorbent composite (3) had a basis weight of 1180 g/m$^2$, a thickness of 1.4 mm, a density of 0.84 g/cm$^3$, and a volume of 42 cm$^3$ and had the anionic absorbent polymer (2) deposited thereon in an amount of 770 g/m$^2$.

Example 4

An absorbent composite (4) of this invention was obtained by repeating the procedure of Example 2 while using the cationic absorbent polymer sheet (3) of Referential Example 3 instead as a cationic absorbent polymer sheet. The absorbent composite (4) had a basis weight of 520 g/m$^2$, a thickness of 1.1 mm, a density of 0.47 g/cm$^3$, and a volume of 33 cm$^3$ and had the anionic absorbent polymer (2) deposited thereon in an amount of 330 g/m$^2$.

Example 5

An absorbent composite (5) of this invention was obtained by repeating the procedure of Example 2 while using the cationic absorbent polymer sheet (5) of Referential Example 5 instead as a cationic absorbent polymer sheet. The absorbent composite (5) had a basis weight of 210 g/m$^2$, a thickness of 0.6 mm, a density of 0.35 g/cm$^3$, and a volume of 18 cm$^3$ and had the anionic absorbent polymer (2) deposited thereon in an amount of 150 g/m$^2$.

Control 1

An aqueous monomer solution consisting of 100 parts of potassium acrylate having a neutralization ratio of 75%, 0.17 part of trimethylol propane triacrylate, 1.24 parts of hydroxyethyl cellulose, 0.29 part of sodium persulfate, and 45.1 parts of water was applied in an amount of 790 g/m$^2$ to a non-woven polyester fabric having a basis weight of 30 g/m$^2$. Then, the non-woven fabric having the aqueous monomer solution deposited thereon was kept in an atmosphere of nitrogen at 120° C. for 3 minutes for inducing the monomer to polymerize to obtain an absorbent composite (1) for comparison having an absorbent polymer fixed to the non-woven fabric. The absorbent composite (1) for comparison was found to have a retaining capacity of 17 g/g.

Control 2

An absorbent composite (2) for comparison was obtained by adding an aqueous cross-linking agent solution consisting of 0.5 part of ethylene glycol diglycidyl ether, 3 parts of water, and 1 part of isopropyl alcohol by spraying to 100 parts of the absorbent composite (1) for comparison obtained in Control 1. The absorbent composite (2) for comparison consequently obtained was found to have a retaining capacity of 15 g/g.

Physical properties of the absorbent composites obtained in Examples 1–5 and Controls 1 and 2 are shown in Tables 1–2.

TABLE 1

|  | Amount of cationic absorbent polymer deposited (g/m$^2$) | Amount of anionic absorbent polymer deposited (g/m$^2$) | Basis weight of absorbent composite (g/m$^2$) |
|---|---|---|---|
| Example 1 | 53 | 327 | 410 |
| Example 2 | 53 | 317 | 400 |
| Example 3 | 380 | 770 | 1180 |
| Example 4 | 160 | 330 | 520 |
| Example 5 | 30 | 150 | 210 |
| Control 1 | — | — | 550 |
| Control 2 | — | — | 590 |

TABLE 2

|  | Retaining capacity (g/g) | Absorbing capacity under pressure (g/g) | Absorption speed (sec.) | Vertical aspiration power (cm) | Gurley stiffness (mgfN) | |
|---|---|---|---|---|---|---|
|  |  |  |  |  | Temperature: 70° C. Humidity: 50% | After drying at 70° C. for 3 hours |
| Example 1 | 30 | 11 | 42 | 4.0 | — | — |
| Example 2 | 30 | 33 | 34 | 8.5 | 60 | 90 |
| Example 3 | 21 | 25 | 97 | 9.5 | 187 | 950 |
| Example 4 | 24 | 29 | 45 | 9.0 | 139 | 270 |
| Example 5 | 27 | 27 | 19 | 6.6 | 60 | 60 |
| Control 1 | 17 | 13 | 99 | 1.8 | — | — |
| Control 2 | 15 | 18 | 106 | 4.0 | 310 | 12000 |

Example 6

Absorbent articles (1)–(5) of this invention were produced by interposing the absorbent composites (1)–(5) produced in a fixed size of 12 cm×25 cm in Examples 1–5 respectively between a polyethylene film, 12 cm×25 cm, having a basis weight of 30 g/m$^2$ and a spun-bond non-woven fabric, 12 cm×25 cm, made of polypropylene fibers and having a basis weight of 30 g/m$^2$ (having a sheet of paper, 30 g/m$^2$ in basis weight, attached to the rear side, namely the absorbent composite side, so as to be used as a surface material on top of the structure to be ultimately formed). Separately, absorbent articles (1) and (2) for comparison were produced by repeating the same procedure while using the absorbent composites (1) and (2) for comparison instead.

A metal plate, 15 mm in thickness, 7 kg in weight, and 14 cm×25 cm in surface area, provided at the center thereof with an opening, 23 mm in diameter, was mounted on the front material of each of the produced absorbent material. Through the opening, physiological saline solution was injected into the absorbent article three times at intervals of 30 minutes. The metal plate was removed 5 minutes after the end of the third injection. A doubled total of 10 kitchen towels, 22 cm×23 cm in surface area and 40 g/m² in basis weight, was mounted on the surface material and the metal plate was placed on the doubled kitchen towels for 1 minute. Then, the kitchen towels wet with the physiological saline solution were weighed to find the amount of rewet (g). The results are shown in Table 3.

TABLE 3

| Sample | Amount of rewet (g) |
| --- | --- |
| Absorbent article (1) | 15 |
| Absorbent article (2) | 4 |
| Absorbent article (3) | 0 |
| Absorbent article (4) | 2 |
| Absorbent article (5) | 8 |
| Absorbent article (1) for comparison | 60 |
| Absorbent article (2) for comparison | 34 |

Example 7

An absorbent composite (6) of this invention was separately obtained by following the procedure of Example 2. The absorbent composite (6) thus obtained had a basis weight of 300 g/m², a thickness of 0.7 mm, a density of 0.43 g/cm³, and a volume of 21 cm³ and had the absorbent polymer particles attached thereto in an amount of 200 g/cm².

Example 8

An absorbent composite (7) of this invention was obtained by following the procedure of Example 1 while using the anionic absorbent polymer (3) of Referential Example 8 as an anionic absorbent polymer instead. The absorbent composite (7) thus obtained had a basis weight of 300 g/m², a thickness of 0.7 mm, a density of 0.43 g/cm³, and a volume of 21 cm³ and had the anionic absorbent polymer (3) attached thereto in an amount of 200 g/cm².

Example 9

An absorbent composite (8) of this invention, 1.0 mm in thickness and 0.6 g/cm³ in density, was produced by superposing two absorbent composites (6) obtained in Example 7, interposing them between acrylic plates, pressing the resultant composite under a pressure of 5 kgf/cm² for one minutes with a simplified press, 17 cm in cross section of the working surface, and then applying cellulose powder (produced by Watman Bio Systems Ltd. and marketed under product code of "CF11") to the surface of the compressed composite in an amount of 30 g/m².

Example 10

An absorbent composite (9) of this invention, 1.0 mm in thickness and 0.58 g/cm³ in density, was produced by repeating the procedure of Example 9 while using two absorbent composites (7) obtained in Example 8 instead.

Example 11

An absorbent composite (10) of this invention, 1.5 mm in thickness and 0.77 g/cm³ in density, was produced by repeating the procedure of Example 9 while using four absorbent composites (6) obtained in Example 7 instead.

Example 12

An absorbent composite (11) of this invention, 1.6 mm in thickness and 0.7 g/cm³ in density, was produced by repeating the procedure of Example 9 while using four absorbent composites (7) obtained in Example 8 instead.

Example 13

A cationic absorbent polymer sheet having a cationic absorbent polymer fixed thereto in an amount of 280 g/m² was produced by following the procedure of Referential Example 1 while having an absorbent binder polymerized and attached to a non-woven polyester fabric, 120 g/cm² in basis weight, 75% in compression coefficient of elasticity, and 8 cm in thickness, instead. Then an absorbent composite (12) of this invention, 1.6 mm in thickness and 0.7 g/cm³, was produced by following the procedure of Example 1 while attaching the absorbent polymer particles obtained in Referential Example 7 in an amount of 800 g/m² to the cationic absorbent polymer sheet instead.

Example 14

An aqueous monomer solution consisting of 20 parts by weight of polyethylene imine (aqueous 30% solution) and 0.025 part by weight of ethylene glycol diglycidyl ether was attached in an amount of 417 g/m² to a non-woven polyester fabric, 30 g/m² in basis weight, 72% in compression coefficient of elasticity, and 2 mm in thickness. The non-woven fabric having the aqueous monomer solution attached thereto was kept in an atmosphere of nitrogen at 80° C. for 30 minutes to obtain a cationic absorbent polymer sheet having the cationic absorbent polymer fixed on the non-woven fabric. The cationic absorbent polymer sheet had the absorbent binder attached thereto in an amount of 125 g/m² and a retaining capacity of 5 g/g.

An absorbent composite was produced by cutting a section, 10 cm×30 cm in surface area, from the cationic absorbent polymer sheet obtained as described above, adding the anionic absorbent polymer (2) obtained in Referential Example 7 to the cut section throughout the entire surface area, and compressing the resultant composite under a pressure of 2 kg/cm² to ensure fast adhesion of the polymer to the cut section. The absorbent composite had a basis weight of 317 g/m², a thickness of 0.7 mm, a density of 0.45 g/cm², and a volume of 21 cm³ and had the anionic absorbent polymer (2) attached thereto in an amount of 162 g/m².

An absorbent composite (13) of this invention, 1.6 mm in thickness and 0.79 g/cm³ in density, was produced by repeating the procedure of Example 9 while using four absorbent composites.

Control 3

In a mixer, 55 parts by weight of the anionic absorbent polymer (2) obtained in Referential Example 7 and 45 parts by weight of ground wood pulp as hydrophilic fibers were dry mixed. An absorbent composite (3) for comparison, 2.0 mm in thickness and 0.60 g/cm³ in density, was produced by uniformly spreading 36 g of the mixture in a frame, 30 cm×10 cm, heating the spread layer of the mixture by spraying (with)water, interposing the resultant sheet of the mixture between acrylic plates, and compressing the produced composite under a pressure of 5 kgf/cm² for one minutes with a simplified press, 17 cm in cross section of the working surface.

Control 4

An absorbent composite (4) for comparison was produced by cutting a section from a commercially available pulp sponge (produced by Nippon Polyester K.K.), 1.8 mm in thickness and 0.44 g/cm³ in density.

Control 5

An aqueous monomer solution consisting of 100 parts by weight of potassium acrylate having a neutralization ratio of 75%, 0.17 part by weight of trimethylol propane triacrylate, 1.24 parts by weight of hydroxyethyl cellulose, 0.29 part by weight of sodium persulfate, and 45.1 parts by weight of deionized water was attached in an amount of 790 g/cm² to an non-woven polyester fabric, 30 g/m² in basis weight and 72% in compression coefficient of elasticity. Then, the non-woven fabric having the aqueous monomer solution attached thereto was kept in an atmosphere of nitrogen at 120° C. for 3 minutes for inducing the monomer to polymerize to obtain a supporting member sheet, 17 g/g in retaining capacity, having the absorbent polymer fixed to the non-woven fabric. An absorbent composite having a retaining capacity of 15 g/g was obtained by adding an aqueous cross-linking agent solution consisting of 0.5 part by weight of ethylene glycol diglycidyl ether, 3 parts by weight of water, and 1 part by weight of isopropyl alcohol by spraying to 100 parts by weight of the supporting member sheet and heat-treating the resultant composite at 100° C. for 30 minutes. An absorbent composite (5) for comparison, 3.0 mm in thickness and 0.69 g/cm³ in density, was produced by superposing four absorbent composites obtained as described above, interposing the superposed absorbent composites between acrylic plates, compressing the produced composite under a pressure of 5 kgf/cm² for one minutes with a simplified press, 17 cm in cross section of the working surface, and then attaching cellulose powder (produced by Watman Bio Systems Ltd. and marketed under product code of "CF11") in an amount of 30 g/m² to the surface of the compressed composite.

Physical properties of the absorbent composites obtained in Examples 9–14 and Controls 3–5 are shown in Table 4 and absorption properties thereof in Table 5.

TABLE 4

| | Base (supporting member) | | | Absorbent polymer | | | Absorbent composite | | | |
|---|---|---|---|---|---|---|---|---|---|---|
| | Basis weight (g/m²) | Thickness (mm) | Compression coefficient of elasticity (%) | Amount of cationic absorbent polymer deposited (g/m²) | Anionic absorbent polymer Deposited amount (g/m²) | Absorbing capacity under pressure (g/g) | Thickness (mm) | Density (g/cm³) | Volume (cm³) | Amount of absorbent polymer (wt %) |
| Example 9 | 60 | 4 | 72 | 140 | 400 | 29 | 1.0 | 0.60 | 30 | 90.0 |
| Example 10 | 60 | 4 | 72 | 140 | 400 | 28 | 1.0 | 0.58 | 30 | 90.0 |
| Example 11 | 120 | 8 | 72 | 280 | 800 | 29 | 1.5 | 0.77 | 45 | 90.0 |
| Example 12 | 120 | 8 | 72 | 280 | 800 | 28 | 1.6 | 0.70 | 48 | 90.0 |
| Example 13 | 120 | 8 | 75 | 280 | 800 | 29 | 1.6 | 0.70 | 48 | 90.0 |
| Example 14 | 120 | 8 | 72 | 500 | 648 | 29 | 1.6 | 0.79 | 48 | 90.5 |
| Control 3 | 520 | 5 | 72 | — | 660 | 18 | 2.0 | 0.60 | 60 | 55.9 |
| Control 4 | — | — | — | — | — | — | 1.8 | 0.44 | 54 | 0 |
| Control 5 | 120 | 8 | 72 | — | 2080 | — | 3.0 | 0.69 | 90 | 94.5 |

TABLE 5

| | Retaining capacity (g/g) | Absorbing capacity under pressure (g/g) | Absorption speed (sec.) | Vertical aspiration power (cm) | Gurley stiffness (gfN) | | Expansion anisotropy | Absorption on inclined plane (sec.) | (g) | Amount of rewet (g) |
|---|---|---|---|---|---|---|---|---|---|---|
| Example 9 | 17 | 24 | 28 | 5.5 | 0.3 | 0.7 | 8.1 | 4 | 28 | 6.0 |
| Example 10 | 21 | 25 | 21 | 6.0 | 0.3 | 0.6 | 9.5 | 5 | 35 | 7.0 |
| Example 11 | 17 | 22 | 28 | 7.0 | 1.9 | 8.9 | 11.1 | 6 | 43 | 1.2 |
| Example 12 | 23 | 24 | 27 | 6.5 | 1.2 | 5.0 | 11.3 | 10 | 66 | 0.2 |
| Example 13 | 18 | 23 | 27 | 7.2 | 1.7 | 7.5 | 12.0 | 7 | 56 | 0 |
| Example 14 | 15 | 22 | 27 | — | — | — | 11.0 | — | — | — |
| Control 3 | 12 | 18 | 17 | ND*1 | 1.2 | 1.4 | ND*1 | 6 | 37 | 8.1 |
| Control 4 | 1.2 | 4 | 1 | 10.0 | 36.6 | 41.6 | 7.2 | 2 | 9 | ND*2 |
| Control 5 | 15 | 16 | 130 | 4 | 18.0 | 54.0 | 2.3 | 2 | 12 | ND*2 |

*1Not determined due to degradation
*2Not determined due to leakage

The absorbent composite according to this invention has a large absorbing capacity under pressure as described above, it allows provision of such absorbent articles as disposable diapers which suffer leakage of liquid only sparingly. Since it has large vertical aspiration power, it can be applied for absorbent articles such as, for example, disposable diapers. It also possesses ample flexibility (as evinced by small Gurley stiffness). When this absorbent composite is used in such absorbent articles as disposable diapers, the absorbent articles fit well to a human body and do not easily deform or warp. Thus the absorbent articles preclude lateral leakage of liquid and permit the wearers to enjoy good feeling of wearing. Further, since the absorbent composite suffers no easy separation of the absorbent polymer, it not only excels in shape-retaining property but also permits a conspicuous decrease in the amount of the supporting member such as of fibrous material. When a sheet of fibers is used as the supporting member, therefore, such absorbent articles as, for example, disposable diapers and sanitary napkins can be produced in extremely small thicknesses.

The absorbent composite of this invention, on absorbing a liquid, expands mainly in the direction of thickness. The absorbent article using this absorbent composite, therefore, does not decrease but rather increases the bulk thereof after it has absorbed a bodily humor and consequently expanded. Thus, the absorbed bodily humor adds to the fitness of the article to the human body and promotes the preclusion of the leakage.

What is claimed is:

1. An absorbent composite comprising a supporting member a cross-linked cationic absorbent polymer fixed to said supporting member and cross-linked anionic absorbent polymer particles fixed to said cross-linked cationic absorbent polymer through an ionic bond.

2. An absorbent composite according to claim 1, wherein the amount of said cationic absorbent polymer is in the range of 1–10,000 parts by weight, based on 100 parts by weight of said supporting member and the amount of said anionic absorbent polymer particles is in the range of 10–10,000 parts by weight, based on 100 parts by weight of said cationic absorbent polymer.

3. An absorbent composite according to any of claims 1–3, wherein said supporting member is a fibrous substance.

4. An absorbent composite in the shape of a sheet having a volume of at least 5 cm$^3$, a thickness of not less than 0.2 mm, and a density in the range of 0.3–1.1 g/cm$^3$ and exhibiting a vertical aspiration power of not less than 5 cm, an absorbing capacity under pressure of not less than 20 g/g, and Gurley stiffness of not more than 1000 mgfN.

5. An absorbent composite according to claim 4, the absorbent composite comprising an absorbent polymer in a proportion of not less than 80% by weight, based on the total weight of said absorbent composite.

6. An absorbent composite containing at least 30% by weight of absorbent polymer based on the total weight of said absorbent composite, wherein said absorbent composite, on absorbing a liquid, shows a value of not less than 3 for the expansion anisotropy specified by the following formula:

expansion anisotropy=$(Ez/Ex+Ez/Ey)/2$ wherein Ex, Ey, and Ez respectively represent the coefficient of linear expansion in the directions of an X axis, Y axis, and Z axis.

7. An absorbent composite according to claim 6, wherein said expansion anisotropy is not less than 5.

8. An absorbent composite according to claim 6, wherein said absorbent polymer is fixed through a medium of an absorbent binder to a supporting member and compressed in the direction of thickness of said absorbent composite.

9. An absorbent composite according to claim 8, wherein said absorbent binder exhibits a retaining capacity of not less than 5 g/g after undergoing centrifugal separation of physiological saline solution.

10. An absorbent composite according to claim 8, wherein said absorbent binder is a cationic absorbent polymer and said absorbent polymer is an anionic absorbent polymer.

11. An absorbent article comprising an absorbent composite set forth in claim 1.

12. An absorbent composite according to claim 1, wherein the amount of said cationic absorbent polymer is in the range of 1–10,000 parts by weight, based on 100 parts by weight of said supporting member and the amount of said anionic absorbent polymer particles is in the range of 10–10,000 parts by weight, based on 100 parts by weight of said cationic absorbent polymer.

13. An absorbent composite according to claim 1, wherein said supporting member is a fibrous substance.

14. An absorbent composite according to claim 2, wherein said supporting member is a fibrous substance.

15. An absorbent composite according to claim 7, wherein said absorbent polymer is fixed through a medium of an absorbent binder to a supporting member and compressed in the direction of thickness of said absorbent composite.

16. An absorbent composite according to claim 9, wherein said absorbent binder is a cationic absorbent polymer and said absorbent polymer is an anionic absorbent polymer.

17. An absorbent article comprising an absorbent composite set forth in claim 1.

18. An absorbent article comprising an absorbent composite set forth in claim 2.

19. An absorbent article comprising an absorbent composite set forth in claim 3.

20. An absorbent article comprising an absorbent composite set forth in claim 4.

21. An absorbent article comprising an absorbent composite set forth in claim 5.

22. An absorbent article comprising an absorbent composite set forth in claim 6.

23. An absorbent article comprising an absorbent composite set forth in claim 7.

24. An absorbent article comprising an absorbent composite set forth in claim 8.

25. An absorbent article comprising an absorbent composite set forth in claim 9.

26. An absorbent article comprising an absorbent composite set forth in claim 10.

* * * * *